April 12, 1955 A. J. ZEBEHAZY Plant Pat. 1,376
AZALEA PLANT
Filed Jan. 20, 1954
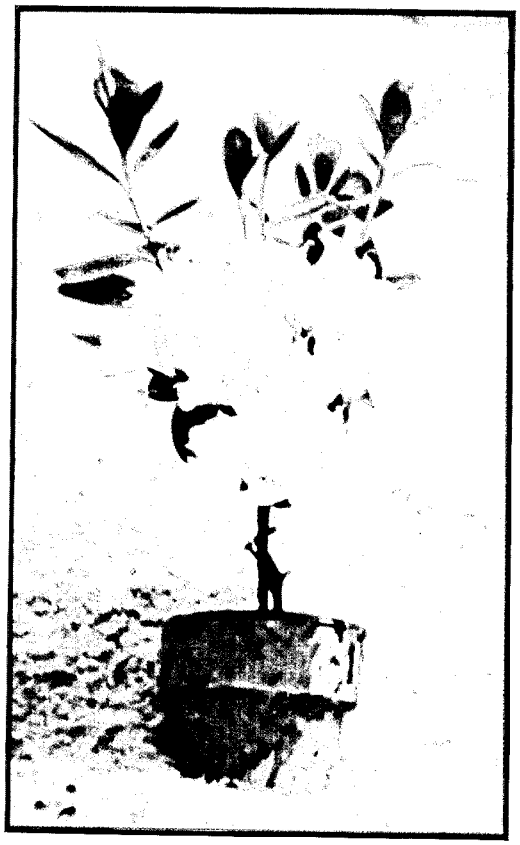
INVENTOR
ALEXANDER J. ZEBEHAZY United States Patent Office Plant Pat. 1,376
Patented Apr. 12, 1955

1,376

AZALEA PLANT

Alexander J. Zebehazy, Painesville, Ohio

Application January 20, 1954, Serial No. 405,271

1 Claim. (Cl. 47—60)

This invention relates to a new and distinct variety of azalea plant belonging to the hardy Japanese hybrid azalea class characterized by generous and late flowering, the flowers being medium large and of intense and brilliant light cherry red or cerise color produced on a plant of spreading yet compact habit. A further advantage of this plant is its extreme hardiness to low temperatures being adapted to withstand temperatures of well below zero.

A still further advantage of this plant is its ready reproduction and early maturity, the plant coming into flower while quite small.

In general, the azalea plant of this invention is excellent for commercial use as a potted plant, as a garden variety, especially in the northern climates because of its evergreen characteristics and hardiness.

This plant was originated and produced by me at my nursery in Painesville, Ohio, as a planned cross of two hardy Japanese hybrids. The two parents are the varieties Gable's Herbert and Fedora, neither of which are patented. Continued asexual reproduction by cuttings at my nursery in Painesville, Ohio, over several seasons of the original plant proved that such variety of azalea plant is fixed in its characteristics and that it is new and distinct.

The accompanying illustration fairly accurately discloses one of these plants in bloom and a close-up view of the flowers, and the following description will give the botanical details.

PLANT CHARACTERISTICS

*Late blooming period.*—By flowering later than azaleas of its class, it definitely and effectively lengthens the azalea blooming season. It blooms just after the hardy Japanese azalea group is through flowering.

*Hardiness.*—As an outdoor garden plant here in northern Ohio, it is hardier than either of its parents which are themselves considered among the hardiest of their class.

*Blooming habit.*—Extremely free flowering, it is completely covered with bloom over the entire plant. There is good lasting quality of the flowers and good resistance to fading from sun and wind.

*Growth habit.*—The plant tends to become broader than it is high, close to the ground, very branched and thickly leaved.

*Flower.*—Color is intense, brilliant and lively. It is attractive from a distance and from nearby.

FURTHER DISTINGUISHING CHARACTERISTICS

*Propagation.*—When reproduced asexually all the distinguishing characteristics come true to form through succeeding propagations. It is easily rooted, and matures readily being able to withstand low temperatures.

Moderately vigorous, dense and symmetrical. Sets buds early and goes into winter well matured.

*Flowering habit.*—More like the azalea Kurume class. It produces a great abundance of flowers. Holds blooms for a long period.

*Adaptation for potting and forcing.*—Due to its compact growth, good leaves, and because even plants of small size flower prolifically, it is well adapted for potting and forcing. Its late flowering period prolongs the potted plant season.

Foliage:

*Size.*—Average 1" to 1¼" in length and ⅝" to ¾" in width.

*Color.*—Medium dark green, bright, approximating color K–7 on Plate 22 in Maerz and Paul Dictionary of Color, 1st edition. In cold weather the leaves assume a bronze tinged coloring.

*Shape.*—Ovate, slightly pointed.

*Texture.*—Firm, evergreen, and generally flat.

Flowers:

*Size.*—2¼" to 2½" across.

*Stem.*—Short and strong.

*Form.*—Hose in hose. Opens out fully and slightly reflexed giving the blossom a wide short trumpet shape.

*Color.*—Bright cerise or light cherry red closely approaching the color J–6 on Plate 1 in the Maerz and Paul Dictionary of Color, 1st edition. Solid.

*Appearance.*—Bright silky sheen.

Reproductive organs:

*Stamens.*—Five, pink in color approximating K–4 shown on Plate 50 in Maerz and Paul.

*Style.*—Well developed, darker than stamens.

*Pollen.*—Freely produced.

I claim:

A new and distinct variety of azalea plant of the hardy Japanese hybrid class, substantially as herein shown and described, characterized by its late blooming habit and hardiness as an evergreen plant, its leaves being generally flat, bright medium dark green in color, ovate in form with a tendency to be pointed, its extreme free flowering with the flowers being medium large, hose-in-hose, of intense light cherry red or cerise color having a silky sheen and its petals being slightly reflexed when the bloom is fully open, both the color of the leaves and of the flowers being substantially resistant to fading of color, by its pleasing low spreading compact growth habit and by its ease of rooting.

No references cited.